(12) United States Patent
Hoornaert et al.

(10) Patent No.: US 10,891,763 B2
(45) Date of Patent: Jan. 12, 2021

(54) ENHANCED IMAGING OF A VASCULAR TREATMENT

(71) Applicant: KONINKLIJKE PHILIPS N.V., Eindhoven (NL)

(72) Inventors: Bart Pierre Antoine Jozef Hoornaert, Arendonk (DE); François Cornelius Johannes Van Daal, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 69 days.

(21) Appl. No.: 15/758,294

(22) PCT Filed: Aug. 31, 2016

(86) PCT No.: PCT/EP2016/070488
§ 371 (c)(1),
(2) Date: Mar. 7, 2018

(87) PCT Pub. No.: WO2017/042068
PCT Pub. Date: Mar. 16, 2017

(65) Prior Publication Data
US 2018/0247437 A1 Aug. 30, 2018

(30) Foreign Application Priority Data
Sep. 10, 2015 (EP) .................................. 15184649

(51) Int. Cl.
*A61B 6/12* (2006.01)
*A61B 34/20* (2016.01)
(Continued)

(52) U.S. Cl.
CPC .............. *G06T 11/005* (2013.01); *A61B 6/12* (2013.01); *A61B 6/486* (2013.01); *A61B 6/504* (2013.01);
(Continued)

(58) Field of Classification Search
None
See application file for complete search history.

(56) References Cited

U.S. PATENT DOCUMENTS 7,941,000 B2   5/2011   Rongen
2008/0137923 A1   6/2008   Spahn
(Continued)

FOREIGN PATENT DOCUMENTS

DE   102007023719 A1   9/2008
EP   2180448 A2   4/2010
(Continued)

OTHER PUBLICATIONS

Tanaka, Nobuhiro et al "Assessment of Optimum Stent Deployment by Stent Boost Imaging: Comparison with Intravascular Ultrasound", Heart Vessels, vol. 28, pp. 1-6, 2013.
(Continued)

*Primary Examiner* — Idowu O Osifade (57) ABSTRACT

An apparatus for determining an enhanced image of a vascular treatment provides (12) a plurality of images including a representation of a region of interest of a vascular structure. Each of the plurality of images includes image data of at least one localizing feature associated with at least one tool configured to be used in the vascular treatment. Each of the plurality of images also includes image data associated with the at least one tool. Registration information for each of the images of the plurality of images is determined (14). At least two images from the plurality of images are selected (16) as a function of the registration information for each of the images. An enhanced image that provides for enhanced visibility of the at least one tool is determined (20). Data representative of the enhanced image is output (24).

17 Claims, 8 Drawing Sheets

(51) Int. Cl.
*G06T 7/00* (2017.01)
*G06T 11/00* (2006.01)
*A61B 6/00* (2006.01)
*G06T 7/38* (2017.01)
*G06T 7/33* (2017.01)
*G06T 7/73* (2017.01)
*A61B 6/03* (2006.01)
*A61B 90/00* (2016.01)

(52) U.S. Cl.
CPC .......... *A61B 6/5235* (2013.01); *A61B 6/5264* (2013.01); *A61B 6/5288* (2013.01); *A61B 34/20* (2016.02); *G06T 7/0016* (2013.01); *G06T 7/33* (2017.01); *G06T 7/38* (2017.01); *G06T 7/74* (2017.01); *A61B 6/032* (2013.01); *A61B 6/4441* (2013.01); *A61B 6/487* (2013.01); *A61B 2034/2065* (2016.02); *A61B 2090/3764* (2016.02); *G06T 2207/10016* (2013.01); *G06T 2207/10081* (2013.01); *G06T 2207/10116* (2013.01); *G06T 2207/20172* (2013.01); *G06T 2207/30021* (2013.01); *G06T 2207/30101* (2013.01)

(56) References Cited

U.S. PATENT DOCUMENTS

| | | |
|---|---|---|
| 2012/0029339 A1 | 2/2012 | Cohen et al. |
| 2012/0134567 A1 | 5/2012 | Baumgart |
| 2012/0140998 A1 | 6/2012 | Zhu |
| 2013/0011041 A1 | 1/2013 | Florent |
| 2016/0174925 A1* | 6/2016 | Dascal ..................... G06T 7/11 382/130 |
| 2019/0220980 A1* | 7/2019 | Ambwani .............. A61B 34/20 |

FOREIGN PATENT DOCUMENTS

| | | |
|---|---|---|
| JP | 2014004465 A | 1/2014 |
| WO | 2003043516 A2 | 5/2003 |
| WO | 2010044001 A2 | 4/2010 |

OTHER PUBLICATIONS http://en.wikipedia.org/wiki/Cardiac_cycle.
https://www.healthcare.siemens.com/angio/options-and-upgrades/clinical-software-applications/clearstent-live/features.
Shinde, Rituparna S. et al "Stent Fracture Detected with a Novel Fluoroscopic Stent Visualization Technique StentBoost", Images in Cardiology, Cancer Journal Cardiology, vol. 25, Aug. 2009.
Tsigkas, Grigorios et al "The StentBoost Imaging Enhancement Technique as Guidance for Optimal Deployment of Adjacent-Sequential Stents", Journal of Invasive Cardiology, vol. 23, No. 10, 2011, pp. 427-429.
Sengupta, P. et al "Twist Mechanics of the Left Ventricle Principles and Application", JACC Cardiovascular Imaging 2008; vol. 1. No. 3.
Buckberg, Gerald et al "Cardiac Mechanics Revisited: The relationship of Cardiac Architecture to Ventricular Function", Circulation 2008, pp. 2571-2587.
http://medicalxpress.com/news/2013-12-software-visualizes-heart-doctors.html.
Achenbach, Stephan et al, "In-Plane Coronary Arterial Motion velocity: measurement with Electron-Beam CT", Radiology, vol. 216, No. 2, 2000, pp. 457-463.
Schoonenberg, G. et al, "Advanced Visibility Enhancement for Stents and Other Devices: Image Processing Aspects" Cardiology Clinic, vol. 27 (2009) 477-490.

* cited by examiner

ENHANCED IMAGING OF A VASCULAR TREATMENT

CROSS-REFERENCE TO PRIOR APPLICATIONS

This application is the U.S. National Phase application under 35 U.S.C. § 371 of International Application No. PCTEP2016/070488, filed on Aug. 31, 2016, which claims the benefit of European Patent Application No. 15184649.0, filed on Sep. 10, 2015. These applications are hereby incorporated by reference herein.

FIELD OF THE INVENTION

The present invention relates to an apparatus for determining an enhanced image of a vascular treatment, to a medical system for determining an enhanced image of a vascular treatment, and to a method for determining an enhanced image of a vascular treatment, as well as to a computer program element and a computer readable medium.

BACKGROUND OF THE INVENTION

In vascular treatments, for example in Percutaneous Transluminal Coronary Angioplasty (PTCA) to treat cardiac stenosis, information relating to the vascular treatments is required to be provided. Imagery, such as that provided on angiographic X-ray projection images is frequently used.

In US2012/0134567A1 an angiographic X-ray imaging system provides enhanced image feature visualization by generating an averaged image from a set of images.

US2013/011041A1 relates to a system and a method for producing an image of a physical object and to a computer program element and a computer readable medium. In order to provide improved stent boost subtract also showing wire state information, a system and a method are provided, the method comprising the following steps: tracking a predetermined first feature and a predetermined second feature in a first plurality of first images, which images reveal a first criterion; and determining a first feature transform; and determining second feature distortion vector fields relative to the first feature transform; associating and recording second feature distortion vector fields corresponding to at least two phase attributes; tracking the predetermined first feature in at least one secondary image which image reveals a second criterion; determining a first-feature-based inter-criterion the first-feature-based inter-phase transform and the second feature distortion vector fields corresponding to a matching phase attribute; and generating a combined inter-criterion image based on the restored physical distortion.

WO03/043516A2 describes that a medical viewing system for displaying a sequence of images of a medical intervention that comprises moving and/or positioning a tool in a body organ, which tool is carried by a support to which at least one marker is attached at a predetermined location with respect to the tool, comprising means for acquiring the sequence of images, and for processing said images during the medical intervention, wherein: extracting means for automatically extracting at least one marker that is attached to the tool support and that neither belongs to the tool nor to the body organ, and yielding the marker location information; computing means for automatically deriving the tool location information from the marker location information, and enhancing means for improving the visibility of the tool and/or the body organ in order to check whether the medical intervention stages are successfully carried out.

US2012/140998A1 describes a method for enhancing stent visibility includes acquiring a set of image frames including multiple test frames. A set of measurement points uniformly distributed within an image of a stent is defined in the test frames. A local image context is defined around each measurement point. A non-rigid deformation field relating the local image contexts of the test frames to local image contexts of a reference image is calculated. The non-rigid deformation field is optimized by maximizing a similarity function between the local image contexts of the test frames and the local image contexts of the reference image. The optimized non-rigid deformation field is used to deform images of a stent in the multiple test frames and combine the non-rigidly deformed images of the stent from the test frames. An image frame with the combined image of the stents superimposed thereon is displayed.

However, implantable cardiac devices, such as stents, and the means by which they are deployed can be difficult to see on angiograms, even when images are provided as averaged images. This means that it can be difficult to deploy a cardiac device at a correct location, such as positioning a stent at the location of a stenosis. It can be difficult to determine if the stent has been correctly deployed, such as being fully expanded. It can be difficult to determine if the stent is broken or is otherwise compromised, such as has a reduced diameter at a position along its length.

SUMMARY OF THE INVENTION

It would be advantageous to have an improved technique for determining an enhanced image of a vascular treatment.

According to a first aspect, there is provided an apparatus for determining an enhanced image of a vascular treatment, comprising:

an input unit;
a processing unit; and
an output unit.

The input unit is configured to provide a plurality of images comprising a representation of a region of interest of a vascular structure. Each of the plurality of images comprises image data of at least one localizing feature associated with at least one tool configured to be used in the vascular treatment and each of the plurality of images comprises image data associated with the at least one tool. The processing unit is configured to determine registration information for each of the images of the plurality of images. The processing unit is also configured to select at least two images from the plurality of images as a function of the registration information for each of the images. The processing unit is also configured to determine an enhanced image from the at least two images, wherein the enhanced image provides for enhanced visibility of the at least one tool. The output unit is configured to output data representative of the enhanced image.

The term "vascular treatment" relates to a procedure that has an effect on the vascular structure in terms of opening width available for blood-flow through the vascular segments. For example, vascular treatment relates to Percutaneous Transluminal Coronary Angioplasty (PTCA), or Percutaneous Coronary Intervention (PCI). For example, the use of interventional devices such as balloons for dilation and stent delivery and detachable coils for aneurysm clotting is provided. In an example, the vascular treatment is to be or has been applied at a location of a stenosis. In an example, the vascular treatment is a revascularization. The vascular treatment, could for example, have been through use of a balloon to open out an artery and deploy a stent.

In this manner, a clinician is provided with the ability to be provided with differing enhanced image information resulting from an acquired image set, relating to different subsets of that acquired imaged set that are used to provide a particular enhanced image. In an example, an enhanced image can be provided that focuses on stabilization of a stent and/or stabilization of stent markers, where for example deformation of the stent geometry can be accepted. In an example, an enhanced image can be provided that focuses on an accurate stent geometry, where for example it will be accepted that the number of images useable to determine a particular enhanced image may come from a relatively small subset of the acquired image set. In other words, the images used to provide the accurate stent geometry may result from images acquired relating to one particular heart cycle phase. Such a fixed phase in the heart cycle can result in images of, for example a stent, with almost identical geometrical properties: the same foreshortening and/or the same twist and/or the same bending. In an example, registration information can relate to such geometrical features of the stent, which could relate to the stent itself or for example markers on a guide wire around which the stent is located. In this manner, images of the stent that are geometrical similar can be combined to provide an enhanced image of the stent, and the actual heart cycle phase need not be known. Similarly, in an example an enhanced image can be provided that focuses on visualization of the struts of a stent, again accepting that the images used to provide the enhanced image may result from images acquired relating to one particular heart cycle phase. Furthermore, in an example, an enhanced image can be optimized for visualization of dedicated tasks, such as visualization of plaque, accepting that the image quality of the stent may be compromised.

In this way an enhanced image is provided that provides for enhanced visibility of a feature, such as a stent and additionally there is a reduction in noise. In an example, the enhanced image enables a better judgment of the geometrical properties of a device. The clinician can, for example, from an acquired image set or run determine if a stenosis has been correctly treated, whether a stent is correctly located, Quantitative Coronary Angiography (QCA) values can be determined at the position of the stent, and it can be determined if a stent has broken. The QCA is the ratio of a smaller diameter segment of a vessel compared to a reference diameter. The reference diameter is the diameter the vessel should have had at that location if it were healthy, and is taken to be the diameters of the vessel spatially either side of the stenosis. Also, the clinician can be provided with an enhanced image that can be used to diagnose plaque quality.

In an example, determining the enhanced image comprises adding at least a part of the at least two images together. In an example, determining the enhanced image comprises averaging at least a part of the at least two images together.

In an example, the processing unit is configured to determine an enhanced image from the at least two images as a function of the at least one localizing feature for each of the images of the at least two images.

The enhanced image being determined as a function of a localizing feature shall be understood as the enhanced image being determined using a localizing feature, such as a marker or markers, as a fixed reference, enabling the images to be combined to provide enhancement in and around the position of the localizing feature and hence the tool.

In an example, the processing unit is configured to determine tool location information for the images of the at least two images as a function of the at least one localizing feature; and to determine an enhanced image from the at least two images as a function of the tool location information. In this manner, the apparatus can be used to provide an improved or enhanced image of the tool.

In an example, the processing unit is configured to determine body element location information for the images of the at least two images as a function of the at least one localizing feature. The processing unit is also configured to determine an enhanced image from the at least two images as a function of the body element location information. In this manner, the apparatus can be used to provide an improved or enhanced image of the region of interest of the vascular structure.

In an example, the registration information comprises the at least one localizing feature. In other words, the position of the at least one localizing feature can be used to select images that are suitable to be used together to provide an enhanced image. For example, as a patient's body moves the at least one localizing feature can move, and this movement of the at least one localizing feature can correlate with the movement of the patient. In other words, during a breathing and/or cardiac cycle the at least one localizing feature can move in a consistent manner, for example as the patient breaths in an out and as the patient's heart beats. Or, to put it another way the at least one localizing feature in an image is representative of the position of the patient's body at the position of the at least one localizing feature when the image was acquired, and this can be used to determine the required registration information used to select images. Then images can be acquired where the region of the patient's body at the location of the at least one localizing feature is similar between those images. In other words, in an example, images can be selected that correspond to the same or substantially the same point in a breathing and/or cardiac cycle that can be used together to provide an enhanced image. Or to put it another way, as the patient breathes and their heart beats, acquired imagery will move. For example, the heart muscles in one chamber of the heart contract and squeeze out blood, while muscles in the other chamber relax and fill with blood. The heart is in effect continually wringing out blood by a twisting motion, like wringing out a mop. Imagery of the vascular system is similarly twisted, with the projected image of vessels, guide wires, stents being foreshortened, bended and twisted continuously. For example, a guide wire, vessel and/or stent can be bent along its length, have part of it brought toward the viewer whilst another part is twisted away (leading to foreshortening), and even suffer twisting along the length. However, by determining registration information comprising the at least one localizing feature, images can be selected that are in the same or similar "twisting" or "wringing" cycle of the cardiac cycle and/or breathing cycle in order that these can be used together to provide the enhanced image. In other words, images that are suffering the same twisting and/or wringing and/or other types of movement can be selected in order that they can be used together to provide the enhanced image.

In an example, the registration information comprises signal data representing a predefined phase of a cardiac cycle. In this manner, a clinician can be provided with an enhanced image relating to a predetermined phase of the cardiac cycle of their choosing.

In an example, the processing unit is configured to select a reference image from the at least two images. The processing unit is also configured to register at least one other image from the at least two images that is not the reference image with the reference image by matching the at least one localizing feature in the at least one other image to the at least one localizing feature in the reference image.

The term "reference image" relates to an image that is being used as a reference or baseline, useable in registering other images to that image. For example, the reference image can be selected as an image within which the at least one localizing feature is represented in a visible and distinct manner, such that the at least one localizing feature can be located and/or identified and/or delineated, either manually or automatically.

In other words, motion compensation can be done by warping image(s) to a specific reference position. To put it another way, an enhanced image is provided with improved visibility due to an increase in contrast of the region of images at the position of the at least one localizing feature with respect to the background structure.

In an example, a storing unit is configured to provide tool and/or vascular structure information relating to the size and/or shape of the tool and/or the size and/or shape of the vascular structure. The processing unit is then configured to determine the registration information as a function of the tool and/or vascular structure information and/or determine the enhanced image from the at least two images as a function of the tool and/or vascular structure information. In other words, the storing unit is configured to store predetermined geometric (tool) configurations such as known (ideal) marker spacing and/or the shape of a correctly deployed stent, and this known information can be used in generating the enhanced image. In this manner, the processing unit can use known information such as the spacing between markers on a guide wire, or the geometry of a stent in for example a correctly deployed state or in various states of deployment in order to facilitate the processing unit in determining the enhanced image.

In an example, the processing unit is configured to determine a plurality of enhanced images as a function of the registration information.

According to a second aspect, there is provided a medical system for determining an enhanced image of a vascular treatment, the system comprising:

an image acquisition unit; and an apparatus for determining an enhanced image of a vascular treatment according to any one of the preceding examples;

The image acquisition unit is configured to acquire the plurality of images.

By providing a medical system for determining an enhanced image of a vascular treatment, the clinician is automatically provided with the required imagery relating to the vascular treatment in order to determine whether such treatment will be or was successful. The clinician can diagnose plaque quality, determine whether a stent is going to be positioned at the correct location, determine whether a stent has been positioned at the correct location, determine if the stent expansion has been adequate and determine if a stent has become broken. The clinician can do this on the basis of an acquired angiogram run, and does not have to resort to other techniques for vascular treatment evaluation such as Intravascular Ultrasound (IVUS), which can increase both the duration and cost of treatment. The clinician can also be provided with data enabling the QCA to be determined accurately.

According to a third aspect, there is provided a method for determining an enhanced image of a vascular treatment, comprising:

a) providing a plurality of images comprising a representation of a region of interest of a vascular structure, wherein each of the plurality of images comprises image data of at least one localizing feature associated with at least one tool configured to be used in the vascular treatment and each of the plurality of images comprises image data associated with the at least one tool;

b) determining registration information for each of the images of the plurality of images;

c) selecting at least two images from the plurality of images as a function of the registration information for each of the images;

e) determining an enhanced image from the at least two images, wherein the enhanced image provides for enhanced visibility of the at least one tool; and f) outputting data representative of the enhanced image.

In an example, the registration information comprises the at least one localizing feature.

In an example, the registration information comprises signal data representing a predefined phase of a cardiac cycle.

In an example, step e) comprises determining an enhanced image from the at least two images as a function of the at least one localizing feature for each of the images of the at least two images.

In an example, the method comprises:

d) selecting a reference image from the at least two images; and wherein step e) comprises registering at least one other image from the at least two images that is not the reference image with the reference image by matching the at least one localizing feature in the at least one other image to the at least one localizing feature in the reference image.

According to another aspect, there is provided a computer program element controlling apparatus as previously described which, in the computer program element is executed by processing unit, is adapted to perform the method steps as previously described.

According to another aspect, there is provided a computer readable medium having stored the computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
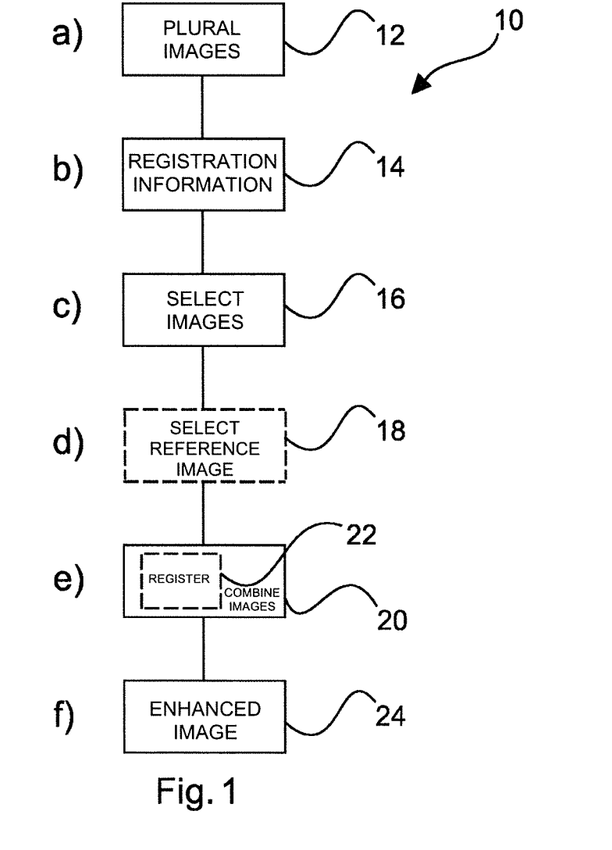
FIG. 1 shows an example of a method for determining an enhanced image of a vascular treatment.

FIG. 1 shows a method 10 for determining an enhanced image of a vascular treatment in its basic form. The method comprises the following:

In a providing step 12, also referred to as step a), a plurality of images comprising a representation of a region of interest of a vascular structure is provided. Each of the plurality of images comprises image data of at least one localizing feature associated with at least one tool configured to be used in the vascular treatment and each of the plurality of images comprises image data associated with the at least one tool.

In a first determining step 14, also referred to as step b), registration information for each of the images of the plurality of images is determined.

In a selecting step 16, also referred to as step c), at least two images from the plurality of images are selected as a function of the registration information for each of the images.

In a second determining step 20, also referred to as step e), an enhanced image from the at least two images is determined. The enhanced image provides for enhanced visibility of the at least one tool.

In an outputting step 24, also referred to as step f), data representative of the enhanced image is output.

In an example, step e) comprises determining an enhanced image from the at least two images as a function of the at least one localizing feature for each of the images of the at least two images.

In an example, the processing unit is configured to determine tool location information for the images of the at least two images as a function of the at least one localizing feature; and to determine an enhanced image from the at least two images as a function of the tool location information.

In an example, the enhanced image comprises an enhanced image of the tool. In this manner, the apparatus can be used to provide an improved or enhanced image of the tool.

In an example, the processing unit is configured to determine body element location information for the images of the at least two images as a function of the at least one localizing feature; and to determine an enhanced image from the at least two images as a function of the body element location information.

In an example, the body element location information comprises vascular structure location information such as the geometric layout of the vascular structure.

In an example, the enhanced image comprises an enhanced image of the vascular structure. In this manner, the apparatus can be used to provide an improved or enhanced image of the region of interest of the vascular structure.

In an example, the method comprises the step of determining feature location information for each of the images of the at least two images as a function of the at least one localizing feature for each of the images of the at least two images. In an example, step e) comprises determining an enhanced image from the at least two images as a function of the feature location information for each of the images of the at least two images.

In an example, the processing unit is configured to determine tool location information for the images of the at least two images as a function of the feature location information; and to determine an enhanced image from the at least two images as a function of the tool location information.

In an example, the processing unit is configured to determine body element location information for the images of the at least two images as a function of the feature location information; and to determine an enhanced image from the at least two images as a function of the body element location information.

In an example, the registration information for an image of the plurality of images is associated with a time of acquisition for the image of the plurality of images.

According to an example, the registration information comprises the at least one localizing feature.

According to an example, the registration information comprises signal data representing a predefined phase of a cardiac cycle.

According to an example, the registration information comprises geometrical characteristics or information. For example, the registration information can relate to the position of one or more markers, and/or relate to the shape of a segment of guide wire, and/or relate the shape of a stent, and/or relate to the position of a stent in the plurality of images. In other words, a subset of images can be selected based on a similarity of marker positions, on a similarity of the bending or position of a guide wire or on a similarity of the bending or position of a stent for example.

According to an example, the method comprises:

In a second selecting step 18, also referred to as step d), a reference image from the at least two images is selected; and wherein step e) comprises registering 22 at least one other image from the at least two images that is not the reference image with the reference image by matching the at least one localizing feature in the at least one other image to the at least one localizing feature in the reference image.

Figure 2:
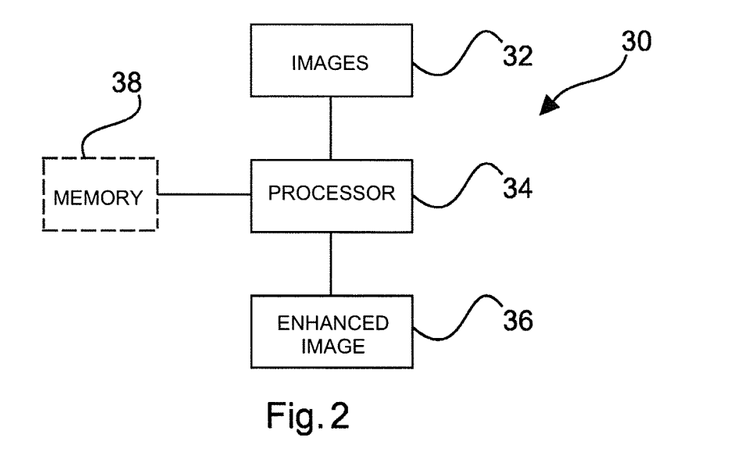
FIG. 2 shows a schematic set up of an example of an apparatus for determining an enhanced image of a vascular treatment.

FIG. 2 shows an example of an apparatus 30 for determining an enhanced image of a vascular treatment. The apparatus comprises an input unit 32, a processing unit 34; and an output unit 36. The input unit 32 is configured to provide the processing unit 34 with a plurality of images comprising a representation of a region of interest of a vascular structure. Each of the plurality of images comprises image data of at least one localizing feature associated with at least one tool configured to be used in the vascular treatment and each of the plurality of images comprises image data associated with the at least one tool. The processing unit 34 is configured to determine registration information for each of the images of the plurality of images. The processing unit 34 is also configured to select at least two images from the plurality of images as a function of the registration information for each of the images. The processing unit 34 is further configured to determine an enhanced image from the at least two images. The enhanced image provides for enhanced visibility of the at least one tool. The output unit 36 is configured to output data representative of the enhanced image.

In an example, the plurality of images comprises angiograms. In an example the plurality of images comprises 150 images acquired over a 10 second run. In other examples, the plurality of images comprises differing numbers of images acquired at differing frame rates. In an example, the plurality of images comprises fluorescence image data.

In an example, the tool comprises a guide wire. In an example, the tool comprises a catheter. In an example, the tool comprises a monorail. In an example, a monorail is introduced by way of a catheter and a guide wire. In an example, the tool comprises a balloon. In an example, the tool comprises a balloon attached to a monorail. In an example, the tool comprises a deflated balloon. In an example, the tool comprises an inflated balloon. In an example, the tool comprises a stent. In an example, the tool comprises a stent tightly wrapped around a balloon. In an example, the tool comprises a stent wrapped around a deflated balloon. In an example, the tool comprises a stent wrapped around an inflated balloon. In an example, the tool comprises a stent that has been deployed through inflation of a balloon. In an example, the tool comprises a stent that has been deployed through inflation of a balloon and where the stent is not wrapped around the balloon.

In an example, the at least one localizing feature comprises a guide wire. In an example, the at least one localizing feature comprises a distil end of a guide wire. In an example, the at least one localizing feature comprises a marker. In an example, the at least one localizing feature comprises a marker on a guide wire. In an example, the at least one localizing feature comprises two markers on a guide wire spaced apart from each other. In an example, the at least one localizing feature comprises two markers on a guide wire spaced apart from each other by a distance substantially corresponding to a length of a stent. In an example, the at least one localizing feature comprises a marker on a balloon. In an example, the at least one localizing feature comprises two markers on a balloon spaced apart from each other. In an example, the at least one localizing feature comprises two markers on a balloon spaced apart from each other by a distance substantially corresponding to a length of a stent. In an example, the at least one localizing feature comprises a stent. In an example, the at least one localizing feature comprises an end of a stent. In an example, the at least one localizing feature comprises the two ends of a stent. In an example, the at least one localizing feature comprises a side edge of a stent. In an example, the at least one localizing feature comprises an edge on one side of a stent and a second edge on the other side of the stent, the edges being spaced apart by approximately a diameter of the stent. In an example, the at least one localizing feature comprises a marker on a stent. In an example, the at least one localizing feature comprises two markers on a stent spaced apart from each other. In an example, the at least one localizing feature comprises two markers on a stent spaced apart from each other by a distance substantially corresponding to a length of the stent. In an example, the at least one localizing feature comprises an outer contour of a stent, where for example a deformable boundary approach is used to detect the outer contour of the stent.

In an example, the at least one localizing feature comprises the vascular structure of the patient. In an example, the at least one localizing feature comprises plaque. In an example, the at least one localizing feature comprises a body element of the patient, such as a part of the diaphragm or vertebrae. In an example, the at least one localizing feature comprises a stent strut.

In an example, the at least one localizing feature in an image is representative of the position of the patient's body at the position of the at least one localizing feature when the image was acquired.

In an example, registration information can be used to determine a subset of images that have been acquired, which are suitable to be used together to provide an enhanced image. For example, the registration information can relate to the movement of a patient, such as breathing and/or cardiac cycle. Images that were acquired at the same or substantially the same point within a breathing and/or cardiac cycle can then be selected in order to be used together to provide an enhanced image. For example, the registration information can relate to an intrinsic aspect of the acquired image data such as the content of an image or images, and/or relate to an extrinsic aspect of the acquired image data such as relate to an external diagnostic system that is being used to monitor the patient in some manner, such as ECG data, patient pulse, ventricular pressure, and/or time of acquisition of an image or images.

In an example, the output data representative of the enhanced image is the enhanced image. For example, the clinician can be provided with a visual image of a vascular treatment or data such as a QCA value associated with the vascular treatment.

In an example, the processing unit is configured to determine an enhanced image from the at least two images as a function of the at least one localizing feature for each of the images of the at least two images.

In an example, the processing unit is configured to determine feature location information for each of the images of the at least two images as a function of the at least one localizing feature for each of the images of the at least two images.

In an example, the processing unit is configured to determine an enhanced image from the at least two images as a function of the feature location information for each of the images of the at least two images.

In an example, the registration information for an image of the plurality of images is associated with a time of acquisition for the image of the plurality of images.

According to an example, the processing unit is configured to determine tool location information for the images of the at least two images as a function of the at least one localizing feature; and to determine an enhanced image from the at least two images as a function of the tool location information.

In an example, the enhanced image comprises an enhanced image of the tool. In an example, the processing unit is configured to determine tool location information for the images of the at least two images as a function of the feature location information; and to determine an enhanced image from the at least two images as a function of the tool location information.

According to an example, the processing unit is configured to determine body element location information for the images of the at least two images as a function of the at least one localizing feature. The processing unit is also configured to determine an enhanced image from the at least two images as a function of the body element location information.

In an example, the body element location information comprises vascular structure location information such as the geometric layout of the vascular structure. In an example, the enhanced image comprises an enhanced image of the vascular structure. In an example, the processing unit is configured to determine body element location information for the images of the at least two images as a function of the feature location information; and to determine an enhanced image from the at least two images as a function of the body element location information.

According to an example, registration information comprises the at least one localizing feature.

In an example, the registration information comprises the position of the at least one localizing feature. In an example, the registration information comprises the position of the at least one localizing feature in the plurality of images. In an example, the registration information comprises an absolute position of the at least one localizing feature. In an example, the registration information comprises the position of a marker. In an example, the registration information comprises the position of a guide wire. In an example, the registration information comprises the position of a balloon. In an example, the registration information comprises the position of a stent.

In an example, images are acquired at different phases of the cardiac cycle that can have registration information on the basis of which these images are selected by the processing unit to be used in providing an enhanced image, for example where the orientation of a stent or guide wire in those images is the same or similar even though the heart is in differing phases or points in the cardiac cycle. For example, the distance between two markers on a guide wire may be at a maximum in a first image indicating that that there is no foreshortening (or a set amount of foreshortening if the guide wire is angled away from the viewer) of the guide wire and/or a stent that has been deployed at the position of the guide wire. In a second image, corresponding to a different phase of the cardiac cycle the distance between the two markers may again be at the maximum value, again indicating that there is no foreshortening (or the same set amount of foreshortening) and therefore these image can be used together, along with other similar images if necessary, to provide an enhanced image of the guide wire and/or the stent and/or the vascular structure at the position of the guide wire. The guide wire in these two images may be in the same angular orientation, or in a different angular orientation. However, because in both images there is no foreshortening or at least the same or similar foreshortening, in an example the images can be used together to provide an enhanced image. In an example, providing the enhanced image comprises rotation of at least a portion of one image with respect to the other image in providing the enhanced image.

In an example, the at least one localizing feature comprises at least two localizing features and the registration information comprises the positions of the at least two localizing features. In an example, the registration information comprises the relative position of a first of the at least two localizing features with respect to a second of the at least two localizing features. In an example, the registration information comprises the positions of two markers. In an example, the registration information comprises the position of one marker relative to the position of a second marker. In an example, the registration information comprises the absolute positions of two markers. In an example, the registration information comprises the angle between a first marker and a second marker. In an example, the registration information comprises the distance between markers and the angle between markers. In an example, the angle between the markers is the angle between a line drawn between the markers and a boundary edge of the image.

In an example, the registration information comprises the shape of a guide wire. In an example, the registration information comprises the shape and position of a guide wire. In an example, the registration information comprises the shape of a guide wire and the position of a marker. In an example, the registration information comprises the shape of a guide wire and the positions of two markers. In an example, the registration information comprises the shape of a guide wire and the position of a first marker relative to the position of a second marker. In an example, the registration information comprises the shape of a guide wire between markers. In an example, the registration information comprises the angle of the guide wire at the position of a marker on the guide wire. In an example, the angle of a section of guide wire is the angle formed between that section of guide wire and a boundary edge of the image. In an example, the registration information comprises the shape of a side edge of a stent. In an example, the registration information comprises the shape of a side edge of a stent and the positions of two markers. In an example, the registration information comprises the shape of a side edge of a stent and the position of a first marker relative to the position of a second marker. In an example, the registration information comprises the position and/or shape of a distil end of a guide wire. In an example, the registration information comprises the relative position of the at least one localization feature with respect to an anatomical landmark of the patient, for example the diaphragm, vertebrae, spine. In an example, the registration information comprises the position of a strut of the stent. The skilled person will understand from the above information on registration information, that the registration can be any combination of the above and the skilled person would be able to use others means as the registration information if necessary.

In an example, a clinician selects a specific image and identifies the at least one localizing feature in that image and where the at least one localizing feature in that image is the registration information in that image. The processing unit, then uses this information to determine registration information in other images that also relates to the at least one localizing feature identified by the clinician, but now in these other images. In other words, the clinician can control the image enhancement. For example, the clinician can click on one or more markers on an image, or click on a section of guide wire having a particular curvature, or click on the position of the diaphragm of the patient.

According to an example, the registration information comprises signal data representing a predefined phase of a cardiac cycle.

In an example, signal data representing a predefined phase of a cardiac cycle comprises electro cardio graph (ECG) data. In an example, the ECG data relates to the patient undergoing the vascular treatment. In an example, the ECG data relates to a generalized ECG signal. In an example, signal data representing a predefined phase of a cardiac cycle comprises ventricular pressure. In an example, signal data representing a predefined phase of a cardiac cycle enables end-systolic images to be selected and used together to provide the enhanced image. In an example, signal data representing a predefined phase of a cardiac cycle enables end-diastolic images to be selected and used together to provide the enhanced image.

In an example, a clinician is provided with ECG data and determines where within that data cycle an enhanced image is to be provided. In other words, the clinician determines a particular point in the ECG cycle or a range of the ECG cycle, and this determines the registration information. Then, those images that were acquired at that point in the ECG cycle, or over that range of the ECG cycle, are selected and used together to provide the enhanced image.

In an example, the clinician can determine the range of the ECG cycle to be used in determining the registration information. Therefore, the clinician can optimize the enhanced imagery in real time by adjusting or tweaking the point and/or range of the ECG cycle being used to select the images to be used in providing the enhanced image. An equivalent situation applies if for example the clinician is provided with ventricular pressure data.

In an example, ECG data is used to determine a chronological stamp for an enhanced image. In an example, registration information can also comprise the at least one localizing feature, and where for example marker positions have been used to select a subset of images to be used in providing the enhanced image. The ECG data can then be used to place that enhanced image within a particular point or over a range of points in the cardiac cycle. Therefore, another enhanced image, provided on the basis of different at least one localizing feature, for example on the basis of markers separated by a different separation to that for the first enhanced image, can be placed into context with the first enhanced image on the basis of the ECG data for the subset of images used to provide the second enhanced image. In this manner, the signal data representing a pre-defined phase of a cardiac cycle, such as ECG data, can be used to enable the correct chronological display of an enhanced image, and enables an enhanced image to be placed into correct chronological sequence, or into correct cardiac cycle sequence, with another enhanced image.

According to an example, the processing unit is configured to select a reference image from the at least two images. The processing unit is also configured to register at least one other image from the at least two images that is not the reference image with the reference image by matching the at least one localizing feature in the at least one other image to the at least one localizing feature in the reference image.

In an example, the at least one other image from the at least two images that is not the reference image is super-imposed on the reference image. In other words, motion compensation is done by warping images to a specific reference position. Then by averaging (or adding) the images together with the reference image leads to an enhanced image with improved visibility at the location of the at least one localizing feature. In an example, the features at the location of the at least one localizing feature in the different images add to or reinforce one another because image data related to the features is added together. Features elsewhere in the images may have moved from one image to the next, and be at different positions in the images. In an example, when the images are added together these features that are elsewhere do not then add to or reinforce each other.

In an example, the image is enhanced with respect to the visibility of the tool, such as the guide wire, balloon, and/or stent. In an example, the image is enhanced with respect to the vascular structure, such as plaque at a particular location of a patient's vascular structure.

In an example, the at least one other image from the at least two images that is not the reference image is registered with the reference image through warping achieved by an affine transformation consisting of translation, and additionally or alternatively rotation, and additionally or alternatively stretching. Pixel wise averaging of warped images then results in an enhanced image.

According to an example, wherein a storing unit 38 is configured to provide tool and/or vascular structure information relating to the size and/or shape of the tool and/or the size and/or shape of the vascular structure. The processing unit is then configured to determine the registration information as a function of the tool and/or vascular structure information and/or determine the enhanced image from the at least two images as a function of the tool and/or vascular structure information.

For example, this information can be used to aid in reinforcing the robustness of an affine transformation used in the motion compensation.

According to an example, the processing unit is configured to determine a plurality of enhanced images as a function of the registration information.

In an example, the output unit is configured to output image data representative of the plurality of enhanced images. In other words, a clinician is provided with the ability to view a tool such as a guide wire or stent, in an enhanced form, relating to different phases of movement of a patient. For example, the ability to view an enhanced image of a tool such as a guide wire or stent can be provided for different stages of a cardiac cycle. For example, the clinician can verify the integrity of a stent at various stages through a cardiac cycle, where the stent may suffer differing levels of strain and stress over that cycle. For example, the integrity of a stent may appear to be adequate in a phase of the heart cycle when the stent is not being particularly stressed or strained, but in a differing phase of the heart cycle the integrity of the stent may be seen to have been compromised. For example, the stent may be seen to be broken in that enhanced "stressed" image, but seen not to be broken in the enhanced "quiescent" image. In an example, the clinician is similarly provided with the ability to view enhanced images of the vascular structure.

In an example, a clinician can determine which enhanced images to view, or view more than one enhanced image at one time. In an example, one enhanced image may be minimized while another enhanced image is maximized.

Figure 3:
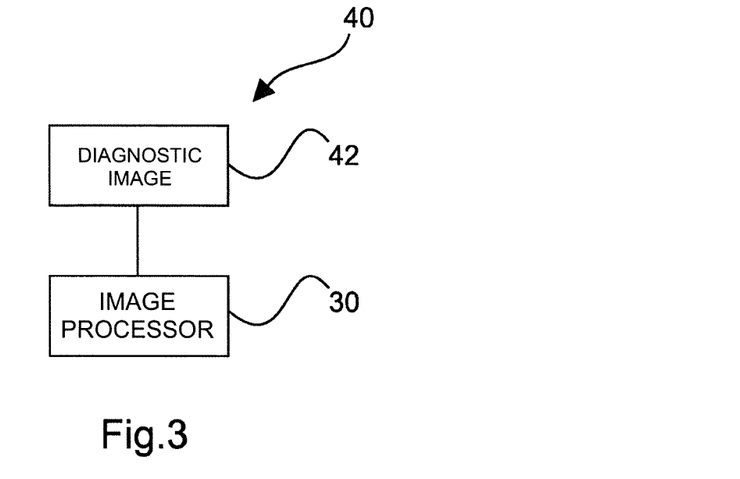
FIG. 3 shows a schematic set up of an example of a medical imaging system for determining an enhanced image of a vascular treatment.
Figure 4:
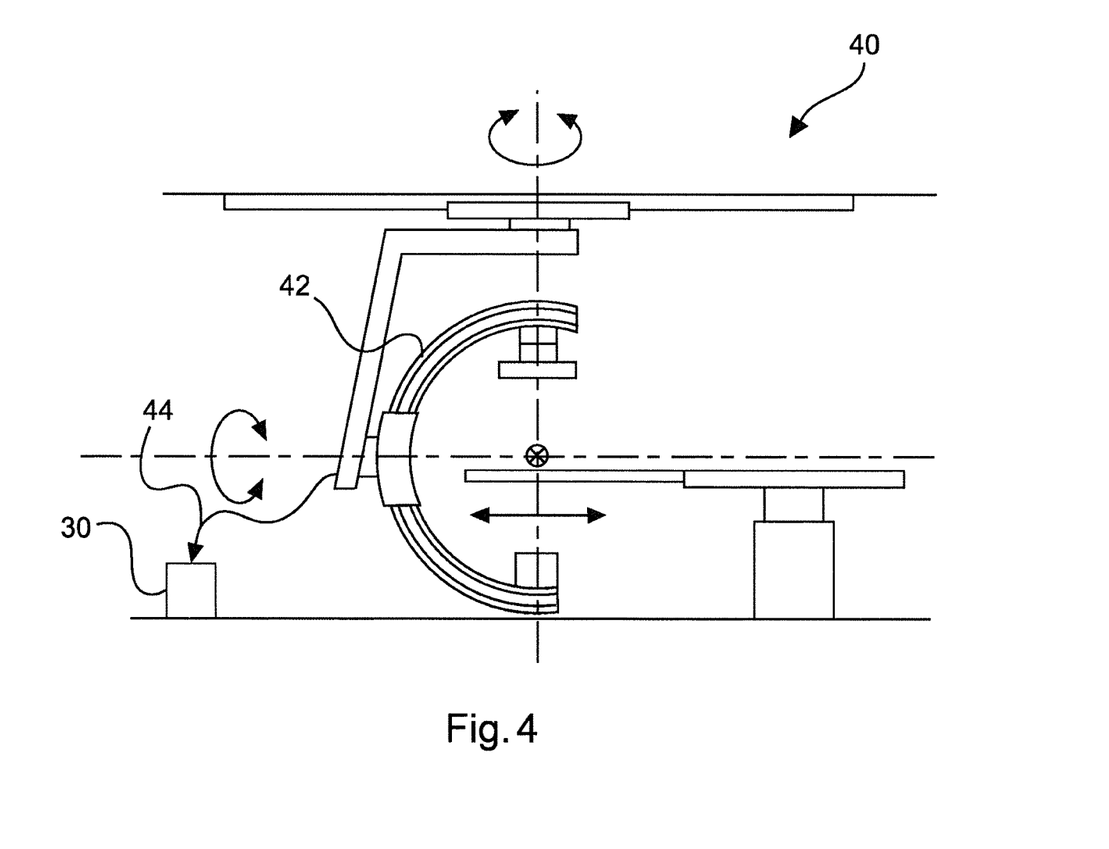
FIG. 4 shows a schematic set up of another example of a medical imaging system for determining an enhanced image of a vascular treatment.

FIG. 3 and FIG. 4 show examples of medical systems 40 for determining an enhanced image of a vascular treatment. The system 40 comprises an image acquisition unit 42, and an apparatus 30 for determining an enhanced image of a vascular treatment provided as an application according to the above mentioned FIG. 2. The image acquisition unit 42 is configured to acquire the plurality of images. The plurality of images is sent from the image acquisition unit 42 to the apparatus 30 via a communication cable 44. In another example, the plurality of images is sent wirelessly. The image acquisition unit 42 is shown as a C-arm angulation arrangement; however in other examples, different types of image acquisition units are used.

In an example, the image acquisition unit comprises an X-ray imaging device. For example, a CT arrangement is provided. For example, the image acquisition unit comprises a C-arm CT system. In an example, the image acquisition unit comprises an interventional X-ray system. In an example, the at least one image acquisition unit comprises a fluoroscopic imaging device, for example a fluoroscopic low-dose X-ray device. In an example, the plurality of images is acquired during fluoroscopic low-dose X-ray surveillance. In an example, the plurality of images is acquired in the manner of an angiogram, but where no, or little, contrast agent has been injected into at least a part of the vascular structure during acquisition of the plurality of images.

In an example, the output data is useable to enable a clinician to determine whether the vascular treatment or intervention was successful.

In an example, the system is used for Percutaneous Transluminal Coronary Angioplasty (PTCA) in catheter laboratories, to treat cardiac stenosis.

Figure 5A:
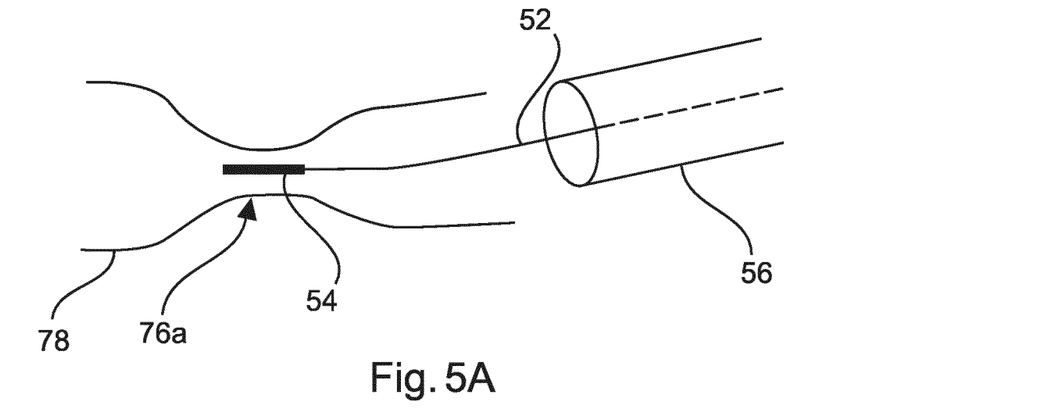
FIG. 5A to FIG. 5F schematically illustrates a vascular treatment.
Figure 5B:
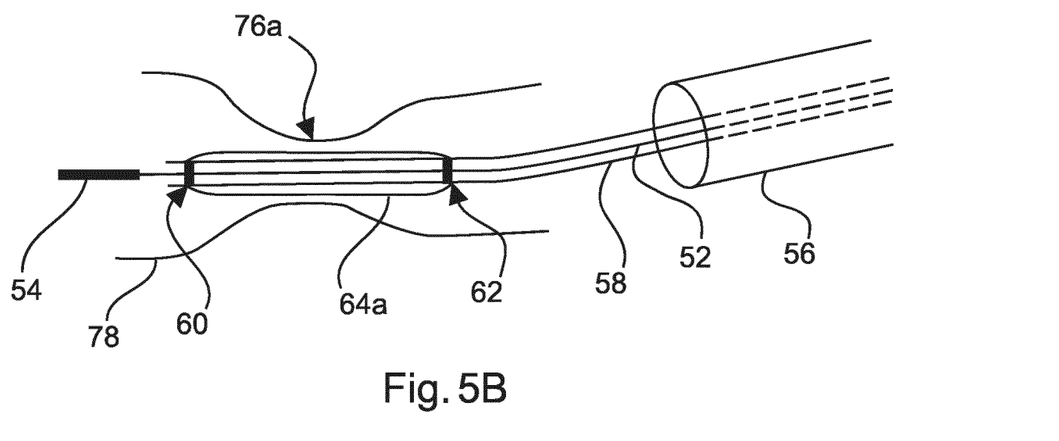
Figure 5C:
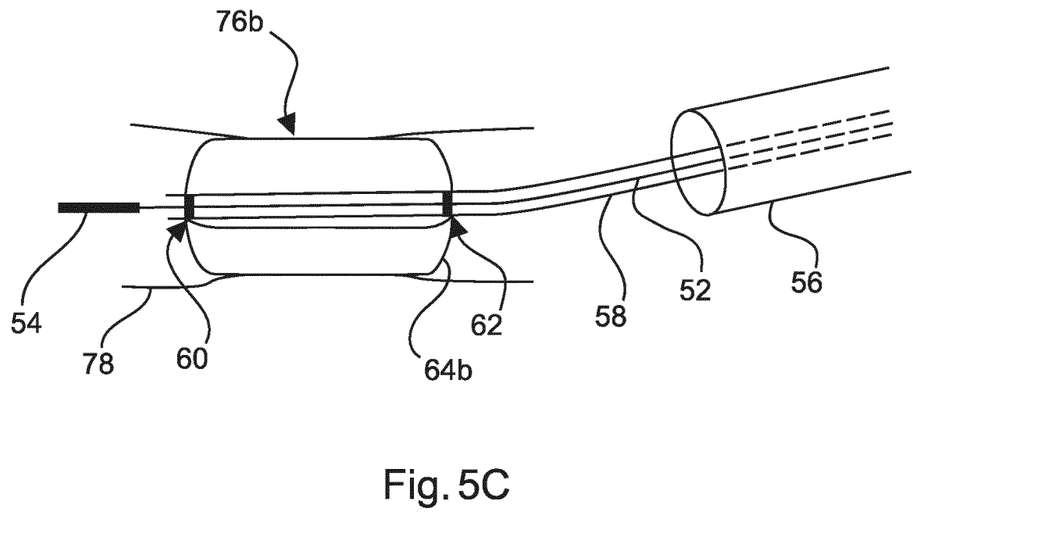
Figure 5D:
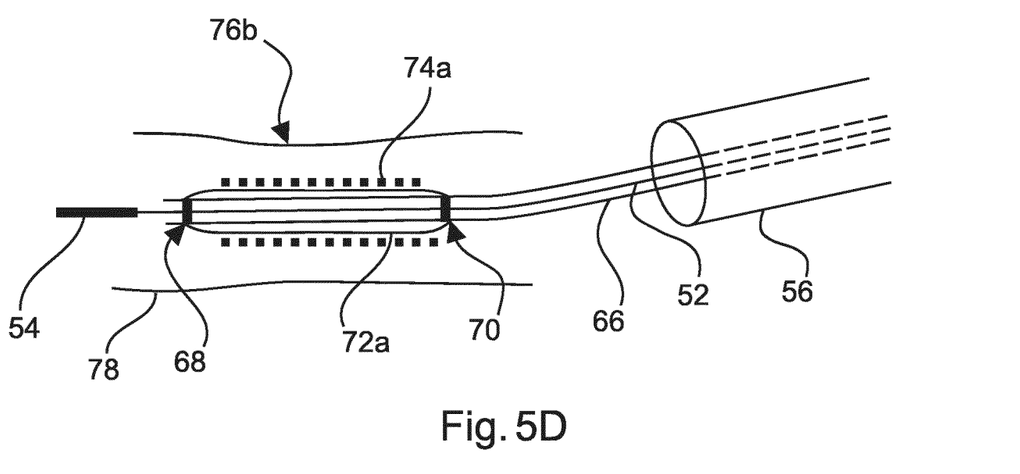
Figure 5E:
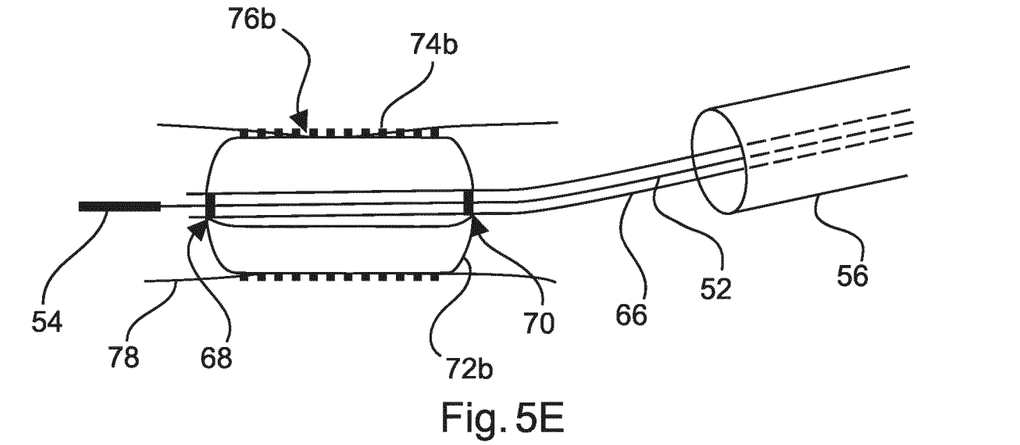
Figure 5F:
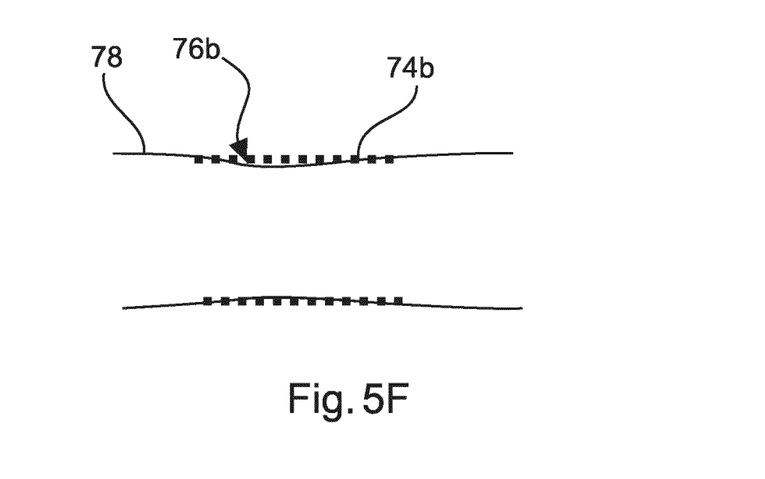

FIG. 5A to FIG. 5F schematically illustrates a vascular treatment, relating to implantation of a stent. The stent implantation is a vascular treatment that usually comprises several stages for enlarging an artery at the location of a lesion called stenosis. In a preliminary stage, the practitioner localizes a stenosis 76a in a patient's artery 78 as best as possible in medical images. This medical intervention includes stages of:

a) Referring to FIG. 5A, introduction in the artery 78, using a catheter 56, of a thin guide-wire 52 that extends beyond the extremity of the catheter 56, and passes through the small lumen of the artery portion 76a at the location of the stenosis.

b) Referring to FIG. 5B, introduction of a monorail 58, which is guided by said guide-wire 52 that passes through the opening of the monorail 58, and which has a first balloon 64a wrapped around its extremity, without stent; and positioning said first balloon 64a in the artery portion 76a at the stenosis location.

c) Referring to FIG. 5C, inflation of this first balloon 64a, which becomes the inflated balloon 64b, for expanding the narrow lumen 76a of the artery 78 at the location of the stenosis to become the enlarged portion 76b of the artery; then, removal of the first balloon 64b with the first monorail 58.

d) Referring to FIG. 5D, again using the catheter 56 and the thin guide-wire 52, introduction of a second monorail 66 with a second balloon 72a wrapped around its extremity, and with a stent 74a around said second balloon 72a; and positioning said second balloon with the stent at the location of the stenosis in the previously expanded lumen 76b of the artery 78.

e) Referring to FIG. 5E, inflation of the second balloon 72a to become the inflated balloon 72b in order to expand the coil forming the stent 74a, which becomes the expanded stent 74b embedded in the artery wall.

f) Referring to FIG. 5F, considering the expanded stent 75b as a permanent implant, and removing the second balloon 72b, the second monorail 66, the guide-wire 52 and catheter 56.

The vascular treatment called angioplasty is difficult to carry out due to badly contrasted medical images, where the guide-wire, balloon, stent and vessel walls are hardly distinguishable on a noisy background and are moreover submitted to motions. Some phases of this intervention are very critical, so checking actions have to be performed during these phases. These phases are:

Phase 1) after stage a) it is important to check the position of the guide-wire 52 with respect to an artery portion of interest 76a, such as the stenosed zone.

Phase 2) between stages b) and c), it is important to check whether the first balloon 64a is placed correctly in coincidence with the stenosed zone 76a of the artery 78.

Phase 3) after stage c), it is important to inspect the artery portion in order to verify the removal of the stenosis by the previous expansion of the first balloon.

Phase 4) between stages d) and e), it is critical to check whether the stent 74a is accurately positioned with respect to the expanded lumen 76b of the artery 78.

Phase 5) After stage e) it is very important to check whether the balloon 72b is sufficiently inflated, and whether the stent 74b is successfully expanded in the artery to be embedded in the artery wall, in order to gauge the result of the operation.

Phase 6) after stage f), it is important to be able to perform checking of the condition of the stent 74b after implantation in the artery portion.

Figure 6:
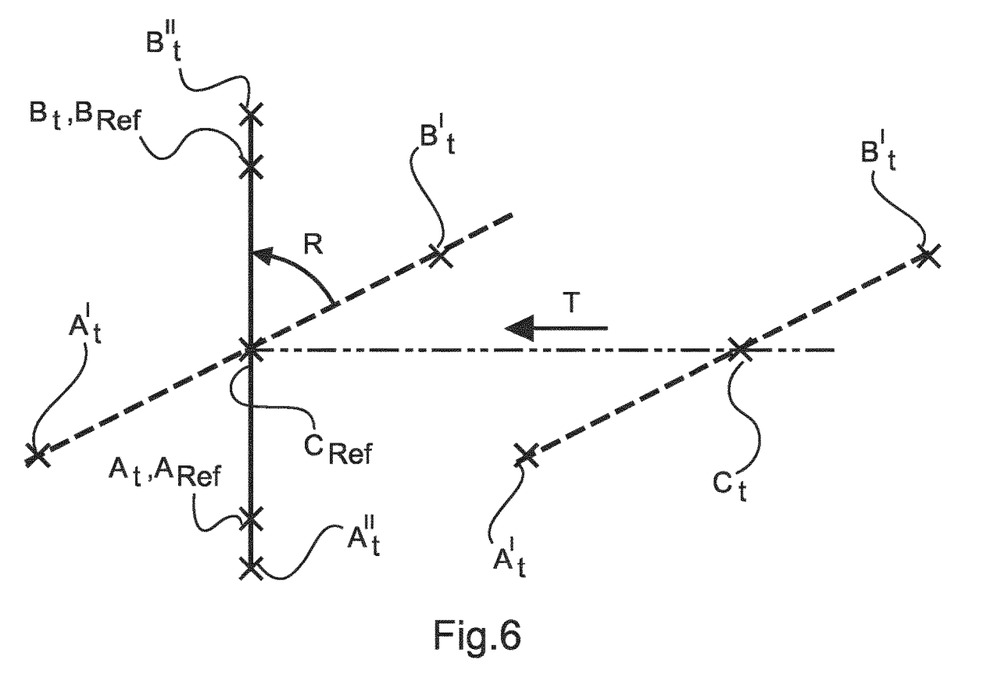
FIG. 6 illustrates an example of a step in determining an enhanced image.

By selecting a subset of acquired image on the basis of registration information, enhanced imagery relating to each of these phases can be provided on the basis of images that can be best used together to provide that enhanced image. This can be done in order that the required feature can be discerned more clearly, with less noise in the image. FIG. 6 illustrates an example of a step in determining an enhanced image. In this example, two markers $A_t$, $B_t$ have been detected in an image of a subset of a sequence of images. The subset of images has already been selected on the basis of registration information. This image is called a reference image, which could be the first image in the subset or any of the images in the subset. Therefore, the markers are termed $A_{Ref}$, $B_{Ref}$. The markers $A_{Ref}$, $B_{Ref}$ may be identified by automatic means, or they could be identified by a clinician. In this example, the markers are selected by through the use of image processing. Image processing then identifies the markers $A'_t$, $B'_t$ in a second image of the subset of the sequence, whether or not the reference markers were determined automatically or manually. Then the second image is registered to the reference image, using the locations of the markers $A_{Ref}$, $B_{Ref}$ in the reference image and the corresponding locations of the markers $A'_t$, $B'_t$ in the second image of the sequence. This operation is performed by matching the markers of the current image to the corresponding markers of the reference image, comprising possible geometrical operations including: A translation T to match a centroid $C_t$ of the segment $A'_t B'_t$ of the current image with a centroid $C_{Ref}$ of the segment $A_{Ref} B_{Ref}$ of the reference image; a rotation R to match the direction of the segment $A'_t B'_t$ of the current image with the direction of the segment $A_{Ref} B_{Ref}$ of the reference image, resulting in a segment $A''_t, B''_t$; and a dilation $\Delta$ for matching the length of the resulting segment $A''_t B''_t$ with the length of the segment $A_{Ref} B_{Ref}$ of the reference image, resulting in the registered segment $A_t, B_t$ for the registered second image. Such operations of translation T, rotation R and dilation $\Delta$ are defined between the images of the subset of the sequence and the reference image, resulting in the registration of the whole sequence. This operation of registration is not necessarily performed on all the points of the images. Zones of interest comprising the markers may be delimited. This operation of registration permits of minimizing the effect of respective movements of the objects of interest, such as vessels, guide-wire, balloons and stent, with respect to a predetermined image referential. In the registered images, the user can easily perform zooming Z on objects of interest. Preferably, two markers, or more, are used for better registration.

Figure 7:
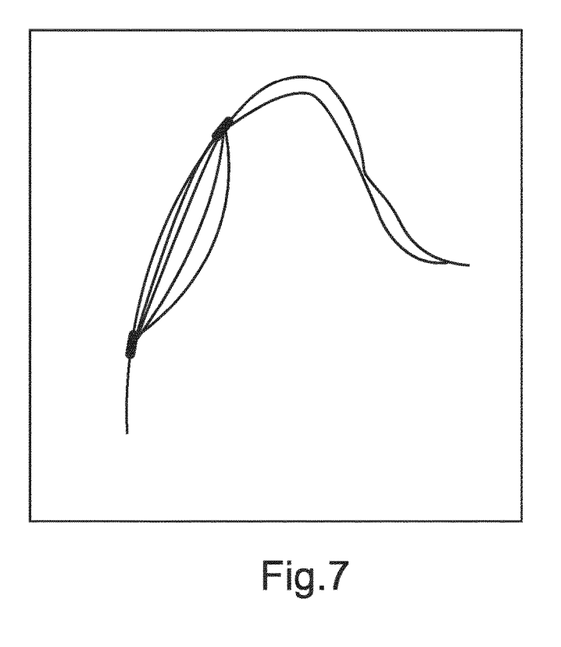
FIG. 7 is a schematic illustration of an image formed from combining a number of images from an image sequence, where registration information has not been used to select specific images from that sequence.
Figure 9:
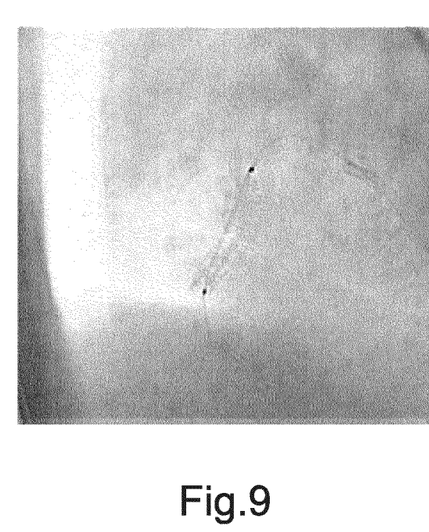
FIG. 9 shows the image represented by the schematic illustration shown in FIG. 7.

In FIG. 7 and FIG. 9, all the images from an image sequence have been combined to form a combined image. The combined image has been determined with two markers used to locate the images at the positions of the two markers. However, because in all the images a stent positioned between the two markers has undergone a number of bending phases, all the different bending phases of the stent have been combined. This has led to image features, other than the two markers, being "washed out".

Figure 8:
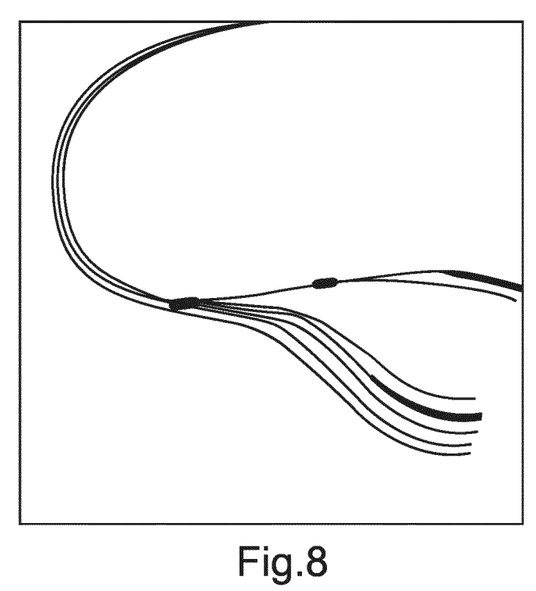
FIG. 8 is a schematic illustration of another image formed from combining a number of images from an image sequence, where registration information has not been used to select specific images from that sequence.
Figure 10:
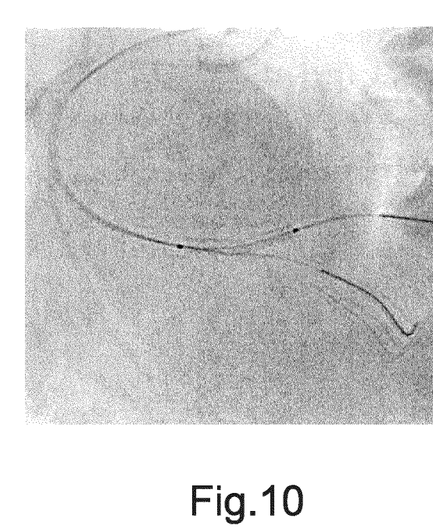
FIG. 10 shows the image represented by the schematic illustration shown in FIG. 8.

Similarly, in FIG. 8 and FIG. 10 all the images from an image sequence have been combined to form a combined image. In the bottom right of the image, multiple positions of a guide wire can be seen, due to the guide wire having moved in the different images with respect to the two markers.

Figure 11:
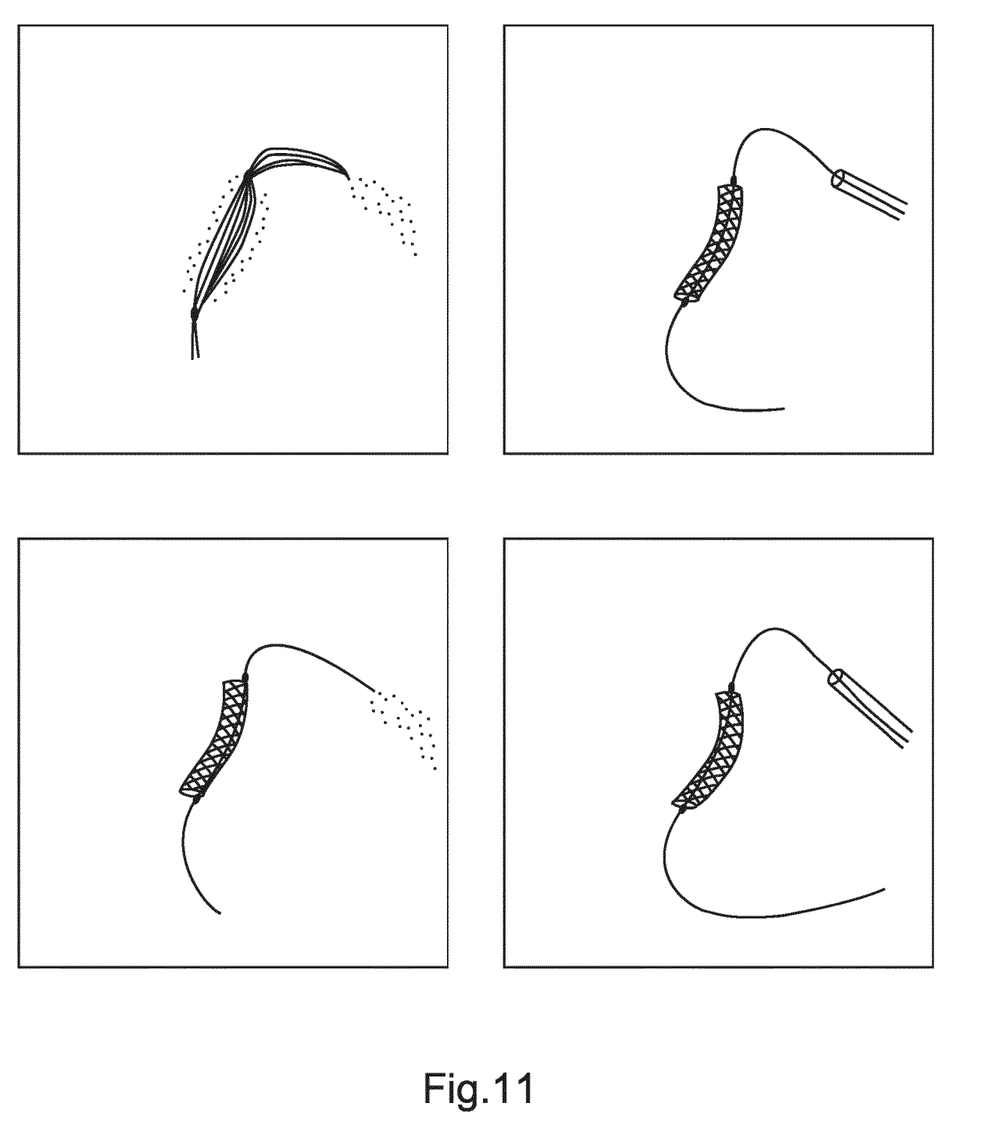
FIG. 11 is a schematic illustration of four images formed from combining a number of images from an image sequence, where in three of those cases registration information has been used to select specific images from that sequence.
Figure 12:
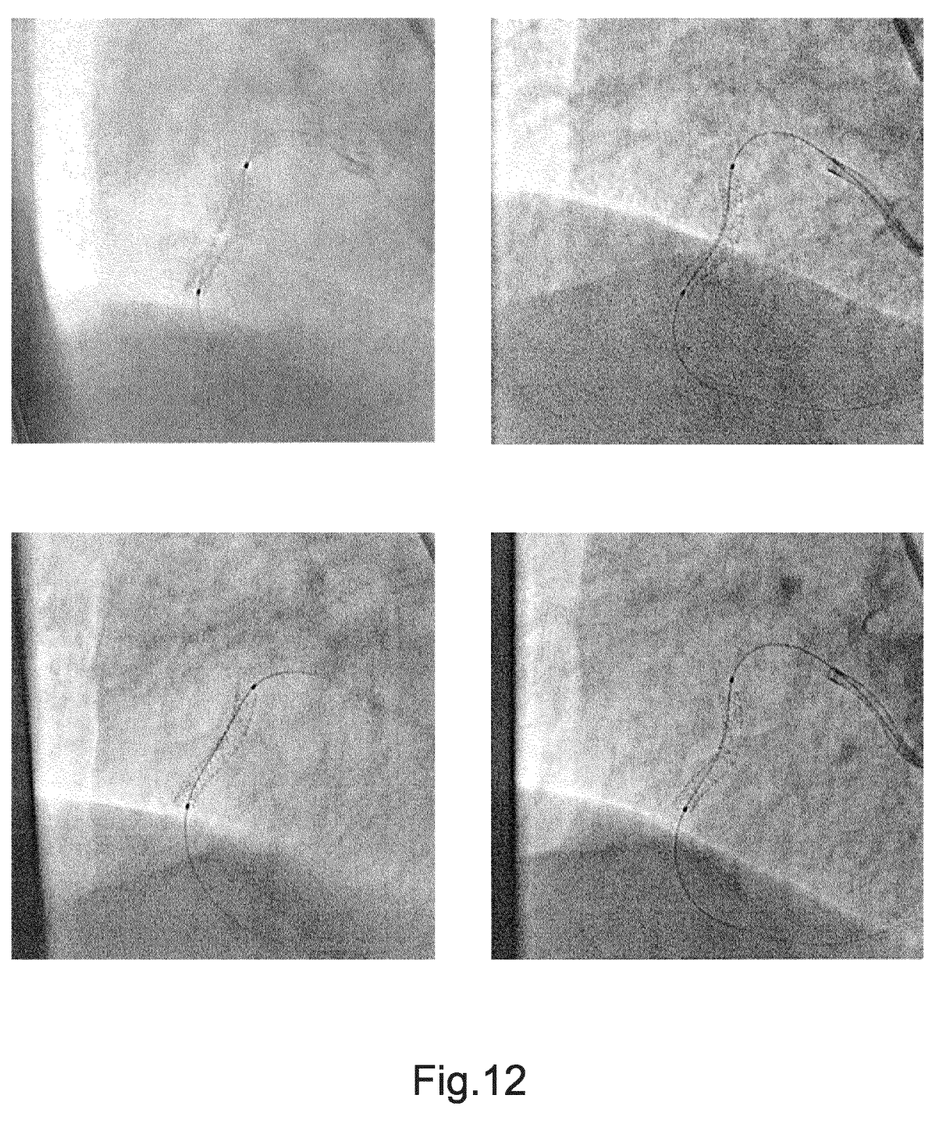
FIG. 12 shows the images represented by the schematic illustrations shown in FIG. 11.

In FIG. 11 and FIG. 12, in the top right image consecutive images from a running image sequence have been combined to form a combined image. This corresponds to FIG. 7 and FIG. 9, where the imagery of a stent has been washed out due to its movement in different images. In the other three images, registration information has been used to select images from the image sequence relating to three different, fixed heart cycle phases. In each case, these selected images have been combined to form an enhanced image. The stent, and indeed stent struts, is clearly discernible in these enhanced images and the guide wire is similarly provided in a clearly discernible manner. The catheter can also clearly be seen. In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for determining an enhanced image of a vascular treatment, comprising:
    a data processor configured to:
        receive a plurality of sets of images generated by the same diagnostic imaging system comprising a representation of a region of interest of a vascular structure wherein the images are contrast agent free, wherein each image of each set of images comprises image data of at least one localizing feature associated with at least one tool configured to be used in the vascular treatment and each image of each set of images comprises image data associated with the at least one tool,
        determine registration information for each of the images of each set of images,
        select a subset of images from each set of images on the basis of the registration information for each of the images, and
        determine an enhanced image of a selectable one or both of the at least one tool and the region of interest of the vascular structure from the subset of images, by combining images of at least a part of the subset of images and wherein the enhanced image provides for enhanced visibility of the at least one tool including:
            (i) determining tool location information from the subset of images as a function of the at least one localizing feature, and determine the enhanced image of the tool from the subset of images based on the tool location information, and/or
            (ii) determining element location information for the subset of images as a function of the at least one localizing feature, and determining the enhanced image of the region of interest of the vascular structure from the subset of images based on the body element location information; and,
    a display device configured to display data representative of the enhanced image.

2. The apparatus according to claim 1, wherein the data processor is further configured to:

determine the enhanced image from the plurality of images as a function of the at least one localizing feature for each of the images of the plurality of images.

3. The apparatus according to claim 1, wherein the registration information comprises the at least one localizing feature.

4. The apparatus according to claim 3, wherein the registration information comprises the position of at least one marker.

5. The apparatus according to claim 3, wherein the registration information comprises the shape of at least one portion of a guide wire.

6. The apparatus according to claim 1,
wherein each set of images includes a plurality of angiographic images of a vascular structure of a patient;
wherein the at least one localizing feature includes a geometric layout of the vascular structure;
wherein the registration information comprises signal data representing a predefined phase of a respiratory or cardiac cycle; and
wherein images in the predefined phase are selected and combined to determine the enhanced image.

7. The apparatus according to claim 5, wherein the data processor is further configured to:
select a reference image from plurality a selected set of images, and
register the other images of the selected set of images that are not the reference image with the reference image by matching the shape of the at least one portion of the guide wire in the other images to the shape of the at least one portion of the guide wire in the reference image to select the subset of images.

8. The apparatus according to claim 6,
wherein a memory is configured to provide tool information relating to the at least one tool; and
wherein the data processor is further configured to determine the enhanced image from each set of images based on the tool information.

9. The apparatus according to claim 7, further including a memory configured to:
provide tool information relating to the at least one tool; and
wherein the data processor is configured to determine the registration information as a function of the tool information.

10. The apparatus according to claim 8, wherein the data processor is further configured to determine a plurality of enhanced images based on the registration information.

11. A medical system for determining an enhanced image of a vascular treatment, the system comprising:
a diagnostic imaging system; and
an apparatus for determining an enhanced image of a vascular treatment according to claim 3;
wherein the diagnostic imaging system is configured to acquire the plurality of sets of images.

12. A contrast agent-free method for determining an enhanced image of a vascular treatment, comprising:

a) providing at least one set of images comprising a representation of a region of interest of a vascular structure, wherein the at least one set of images are free of contrast agents, wherein each of the sets of images comprises image data of at least one localizing feature associated with at least one tool configured to be used in the vascular treatment and each of the sets of images comprises image data associated with the at least one tool;

b) determining registration information for each of the images of each set of images;

c) selecting a subset of images from each set of images on the basis of the registration information for each of the images; and e) determining an enhanced image of the at least one tool from the subset of images by combining at least a part of the subset of images including:
  (i) determining tool location information from the subset of images as a function of the at least one localizing feature, and determine the enhanced image of the tool from the subset of images based on the tool location information, and
  (ii) determining element location information for the subset of images as a function of the at least one localizing feature, and determining the enhanced image of the region of interest of the vascular structure from the subset of images based on the body element location information.

13. A non-transitory computer-readable medium storing a program element, which when executed by a processor is configured to carry out the method of claim 12.

14. The method according to claim 12,
wherein the at least one set of images includes a set of angiographic images of a vascular structure of a patient;
wherein the at least one localizing feature includes a geometric layout of the vascular structure;
wherein the registration information includes at least one of a signal representing cardiac phase, changes in changes in a shape of a portion of a guide wire attributable at least in part to cardiac motion, and changes in a location and orientation of a stent attributable at least in part to cardiac motion; and
wherein determining the enhanced image includes combining images of the subset of images that are in a common cardiac phase and/or the portion of the guide wire has a common shape and/or the stent is in a common location and has a common orientation.

15. An apparatus for determining an enhanced image of a vascular treatment comprising:
one or more processors configured to perform the method according to claim 12.

16. The apparatus according to claim 15, further including a display device configured to display the enclosed images.

17. The method according to claim 12, further including:
providing a plurality of sets of images; and
determining a plurality of enhanced images from the plurality of sets of images.

* * * * *